United States Patent [19]

Palonen et al.

[11] Patent Number: 5,012,501

[45] Date of Patent: Apr. 30, 1991

[54] APPARATUS FOR PRODUCING PANORAMIC X-RAY IMAGE PROJECTIONS

[75] Inventors: Juhani Palonen; Hannu Purhonen, both of Espoo, Finland

[73] Assignee: Instrumentarium Corp., Finland

[21] Appl. No.: 500,181

[22] Filed: Mar. 28, 1990

[30] Foreign Application Priority Data

Sep. 14, 1989 [FI] Finland .................. 894339

[51] Int. Cl.$^5$ ............................................. A61B 6/14
[52] U.S. Cl. ........................................ 378/38; 378/39; 378/168; 378/170; 378/197
[58] Field of Search ............. 378/38, 39, 40, 168, 378/169, 170, 183, 197

[56] References Cited

U.S. PATENT DOCUMENTS

| | | | |
|---|---|---|---|
| 4,039,837 | 8/1977 | Ohta et al. | 378/168 |
| 4,241,254 | 12/1980 | Välilä | 378/168 |
| 4,263,513 | 4/1981 | Palluet | 378/168 |
| 4,599,739 | 7/1986 | Nishikawa et al. | 378/39 |
| 4,661,967 | 4/1987 | Nishikawa | 378/39 |
| 4,783,793 | 11/1988 | Virta et al. | 378/39 |
| 4,856,038 | 8/1989 | Guenther et al. | 378/40 |

FOREIGN PATENT DOCUMENTS

| | | |
|---|---|---|
| 204676 | 12/1986 | European Pat. Off. . |
| 228614 | 7/1987 | European Pat. Off. . |
| 229308 | 7/1987 | European Pat. Off. . |
| 340349 | 11/1989 | European Pat. Off. . |
| 2252578 | 12/1973 | Fed. Rep. of Germany . |
| 66993 | 12/1976 | Finland . |
| 844414 | 11/1984 | Finland . |
| 79459 | 2/1986 | Finland . |

*Primary Examiner*—Edward P. Westin
*Assistant Examiner*—Kim-Kwok Chu
*Attorney, Agent, or Firm*—Andrus, Sceales, Starke & Sawall

[57] ABSTRACT

Apparatus for producing panoramic x-ray image projections of the dental arch on X-ray film. The apparatus includes a fixed body (1). The opposite ends of a movable supporting arm (11) are fitted with an X-ray source (12) and a film holder (13) that may be positioned on opposite sides of the dental arch. A first drive (20-23) produces a rotating motion of supporting arm (11) with respect to the arch. A second drive (2, 4) sets the center of rotating motion in linear movement in dependence on the angular position of supporting arm (11). The apparatus further includes a selector (3, 6, 10) for selecting the direction of linear motion (translatory motion) as desired. The selector includes a rotary plate (3), journalled (9) to the body (1) and to which is journalled (8) a linear plate (2) facilitating the linear motion; a motor (10), which is mounted on the rotary plate (3) and which, by means of its associated pinion and a tooth rim (6) provided on body (1), translates the rotary plate (3) to a desired angular position; and a sensor (19) for the determination of a desired angular position.

4 Claims, 9 Drawing Sheets

APPARATUS FOR PRODUCING PANORAMIC X-RAY IMAGE PROJECTIONS

The present invention relates to an apparatus as set forth in the preamble of claim 1 for producing panoramic X-ray image projections. An object in odontological X-ray imaging is to acquire essential diagnostic information about an object to be imaged. On the other hand, the human denture along with its surrounding tissues is a rather special object to be imaged and, accordingly, sets special requirements for the imaging system. Thus, the situation today is such that there is no available imaging method capable of delivering alone all necessary information but, instead, a parallel application of a plurality of complementary imaging methods and equipment is required.

The most traditional odontological imaging technique is intraoral film imaging. In this method, imaging is effected by placing in the mouth of a patient behind the teeth to be imaged an X-ray film, the size of which is for example 30 mm×40 mm. As the patient uses his or her finger to hold the film in position, a person doing the imaging directs manually the end of an X-ray tube relative to the patient in a manner that a cone of rays defined by a collimator cylinder or cone aligns itself with the film and at a proper angle relative to the teeth to be imaged. This is followed by irradiation. Imaging has been facilitated by making improvements to the method, e.g. by aligning the X-ray film relative to the cone of rays by means of various holders. Nevertheless, the alignment of a cone of rays relative to the patient remains to be visually assessed.

The intraoral film technique has its own benefits: As the X-ray effect a direct exposure of the X-ray film, the resulting X-ray image is extremely sharp and contains abundant information even about minor details. As a matter of fact, such an image contains more information than what could be discerned by the human eye. In certain situations, another benefit is also the fact that imaging can be focused on a certain individual tooth. A major benefit is also that the X-ray only pass through diagnostically interesting tissues and, thus, the film does not contain shadows of other sections of the head.

The drawbacks of intraoral film technique include a relatively high dosage of radiation the patient is subjected to due to the direct exposure of film as well as impracticality if a general picture is desired of the denture and jaws of a patient. It has also become obvious that sometimes the dentist does need information also about such areas that cannot be imaged by using the intraoral film method.

Over the past couple of decades, so-called panoramic tomography imaging has become routine practice along with the above-described imaging method. This method is completely extraoral and an essential feature of the imaging result is that a single continuous panoramic image of the area of the denture and jaws is obtained on film, the size of said image being typically 12-15 cm×30 cm. There are several known apparatus constructions for the application of this method. An example of such equipment is described in GB Patent 1 594 499.

A common feature in such constructions is that, during the imaging session, suitable support and carrier means are used for moving around the head of a patient a combination, comprising an X-ray tubehead along with its means for delimiting the cone of rays as well as a film cassette, mounted on the opposite side of the patient's head relative to said tubehead and containing an X-ray film and a pair of reinforcement plates. A collimated horizontally narrow cone of rays emitting from the tubehead penetrates the patient's head and finds the film cassette subjecting the film to exposure a narrow section at a time. As the cone of rays travels during imaging in a suitable manner relative to the dental arch of a patient, the film cassette travels simultaneously relative to the cone of rays orthogonally thereto. As the cone of rays is forced to travel through the head of a patient, the shadows of skull sections outside the dental arch being imaged are also projected on film. However, these will become out-of-focus or blurred as a result of the tomography effect.

The popularity of panoramic tomography technique is based on benefits being gained in the areas where the intraoral method has its weakneses. A continuous panoramic image transmits information over the entire area of the jaws, thus indicating well also the condition of the tissues surrounding the teeth. Panoramic tomography imaging is also easy and quick to perform. In addition, by virtue of reinforcement plates, the amount of radiation energy delivered to a patient in panoramic imaging is relatively small, matching the amount of energy delivered in the exposure of 2-3 intra-oral films.

But also panoramic tomography technique has its own defects. The resolution of reinforcement plates is not nearly as good as that of a plain X-ray film. Thus, the panoramic images are more out-of-focus than intra-oral film images. This in itself is not a defect, since the the reinforcement plates have a sufficient resolution for delivering the information essential in terms of diagnosis. A serious drawback is, however, that panoramic images include locally some blurring caused by the movement also in such areas which are diagnostically essential. This is due to the fact that in tomographic imaging there is just a certain layer of the object sharply outlined while the other sections are more or less blurred. In dental imaging, the purpose is naturally to coincide this layer with the dental arch of a patient both for its shape and size. In practice, this involves difficulties and primarily for two reasons: First of all, the size and shape of a human dental arch varies from individual to another and it has not been possible to construct properly operating adaptive systems of imaging geometry. Secondly, in panoramic tomography imaging it also necessary to consider the direction of a cone of rays relative to the dental arch. In order to make the cone of rays to penetrate the dental arch roughly in perpendicular direction as well as to make the imaging smoothly continuous, the apparatus designer must make compromises with a consequence that a sharply imaging layer is locally (in the region of incisors) so thin that essential objects are often left outside of it and thus imaged out of focus.

To some extent there is also used such panoramic imaging method wherein the radiation-emitting member of an X-ray tube, i.e. the anode, is placed in the mouth of a patient and the X-ray film contained in a flexible cassette is bent outside the maxilla and submaxilla so as to conform with the skin. Although this method involves no out-of-focus problems, its application has proved inconvenient. In addition, the surface of a patient's tongue and palate is exposed to a relatively high dose of radiation. Neither is the direction of a cone of rays relative to the dental arch in all aspects optimal.

In all the above-described imaging methods there are often problems of imaging the gap between two adjacent teeth i.e. the gap between approximal surfaces as well as the maxillary joints from a proper angle. Unless the cone of rays travels in the same direction as said gap, the adjacent teeth will be imaged partly overlapping. Furthermore, unless the cone of rays travels in parallel or perpendicular direction to the condyle, the image of maxillary joints will be distorted.

An object of the present invention is an imaging method capable of providing information relating to approximal surfaces and maxillary joints more reliably than the prior art methods and wherein benefits of the prior art methods are combined while eliminating drawbacks.

In order to achieve this object, the basis of the invention is an apparatus for producing panoramic X-ray image projections from a dental arch shaped object or a certain section thereof on an X-ray film, said apparatus comprising a fixed body, a movable supporting arm whose opposite ends are fitted with an X-ray source and a film holder on the opposite sides of an object to be imaged, as well as means for setting the supporting arm in a rotating motion around the object, and means for setting the centre of the rotating motion in a linear movement in depence on the angular position of the supporting arm. In order to achieve the above objective, the invention is characterized in that the apparatus further includes means for selecting the direction of linear motion (translatory motion) as desired.

The invention will now be described with reference made to the accompanying drawings, in which.

Figure 1A:
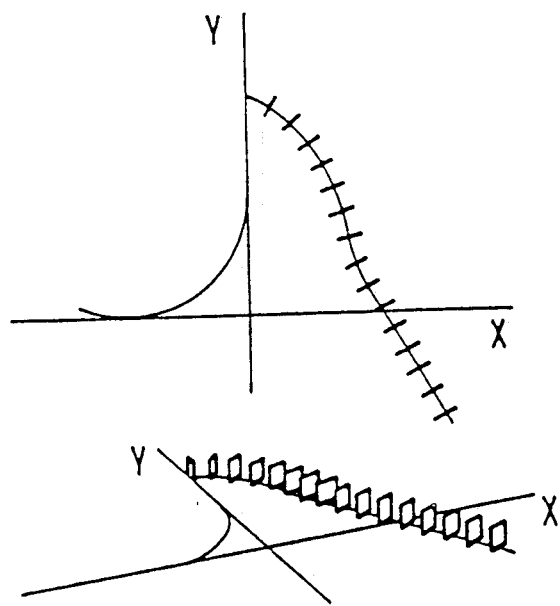
FIG. 1 shows an arrangement for measuring the angle between the direction of rays and the normal of an image layer.
Figure 1B:
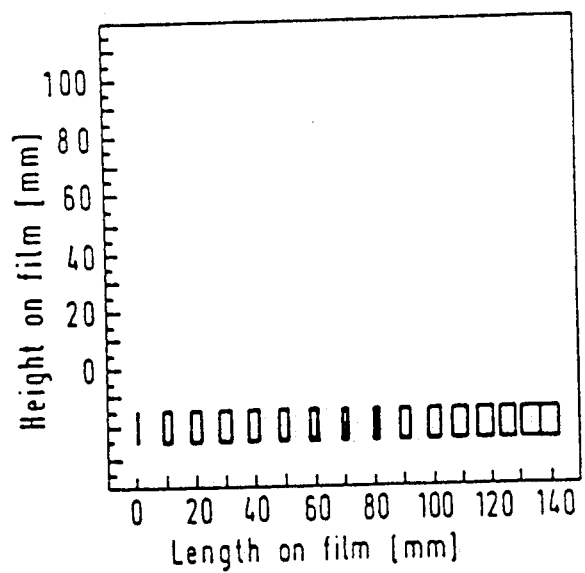
Figure 2:
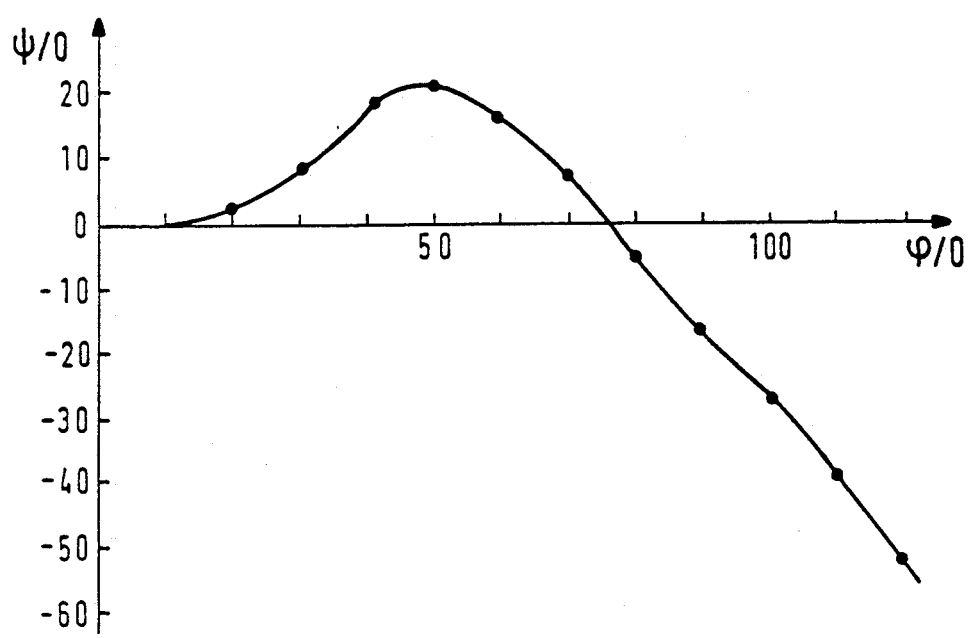
FIG. 2 is a graph showing the measuring results obtained with the arrangement of FIG. 1.
Figure 3:
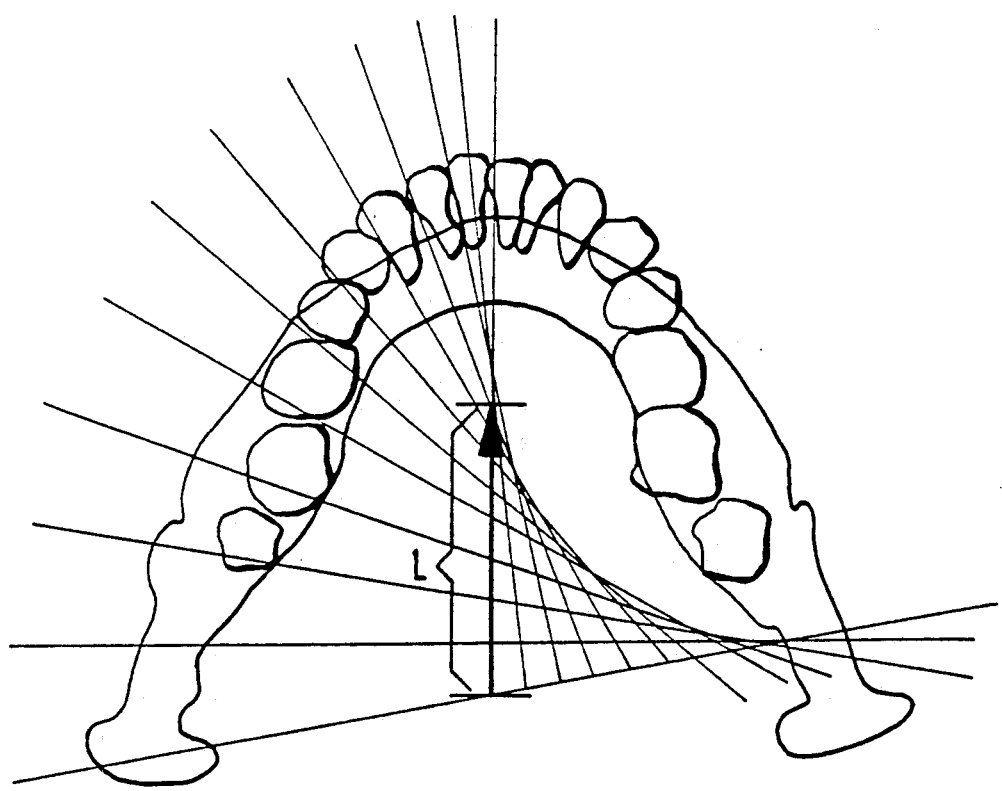
FIG. 3 illustrates the direction and length of linear motion (translatory motion) L in conventional panoramic imaging.
Figure 4:
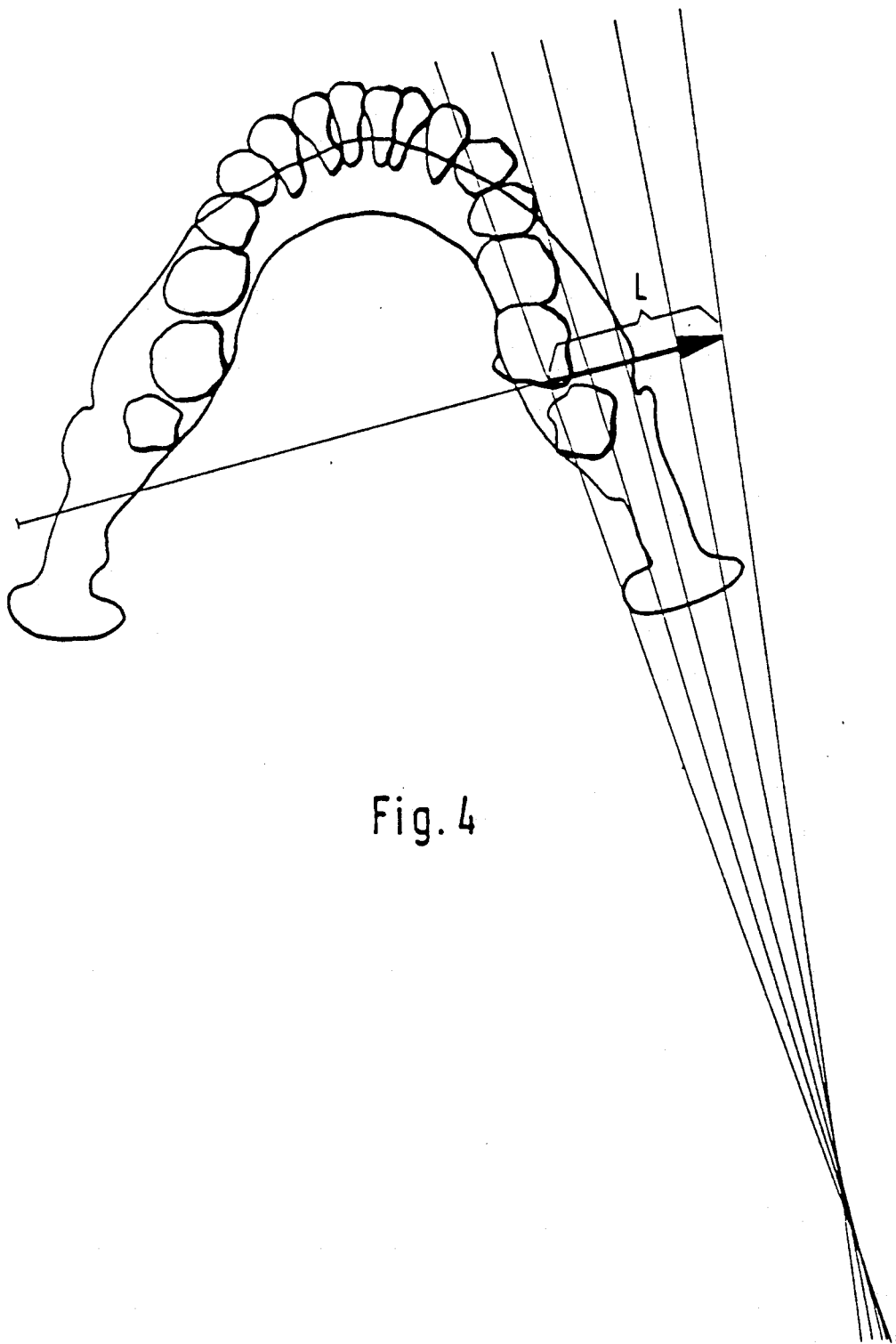
FIG. 4 shows the optimal direction and length for translatory motion in the imaging of the second maxillary joint PA (posteroanterior).
Figure 5:
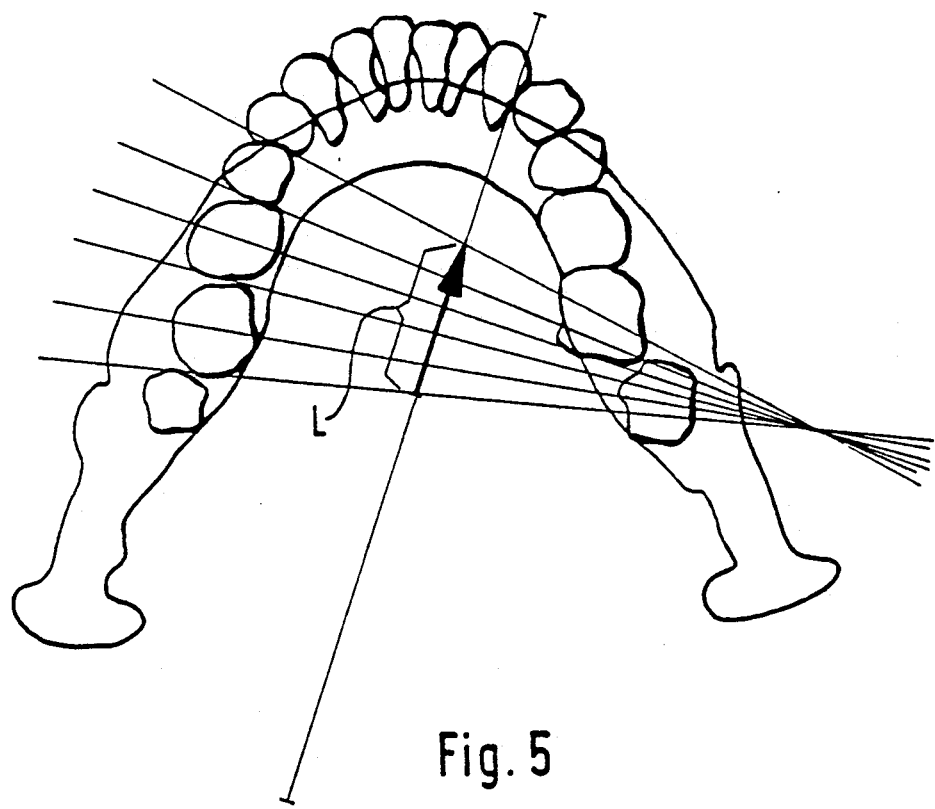
FIG. 5 shows the optimal direction and length for translatory motion in the imaging of molar teeth.
Figure 6:
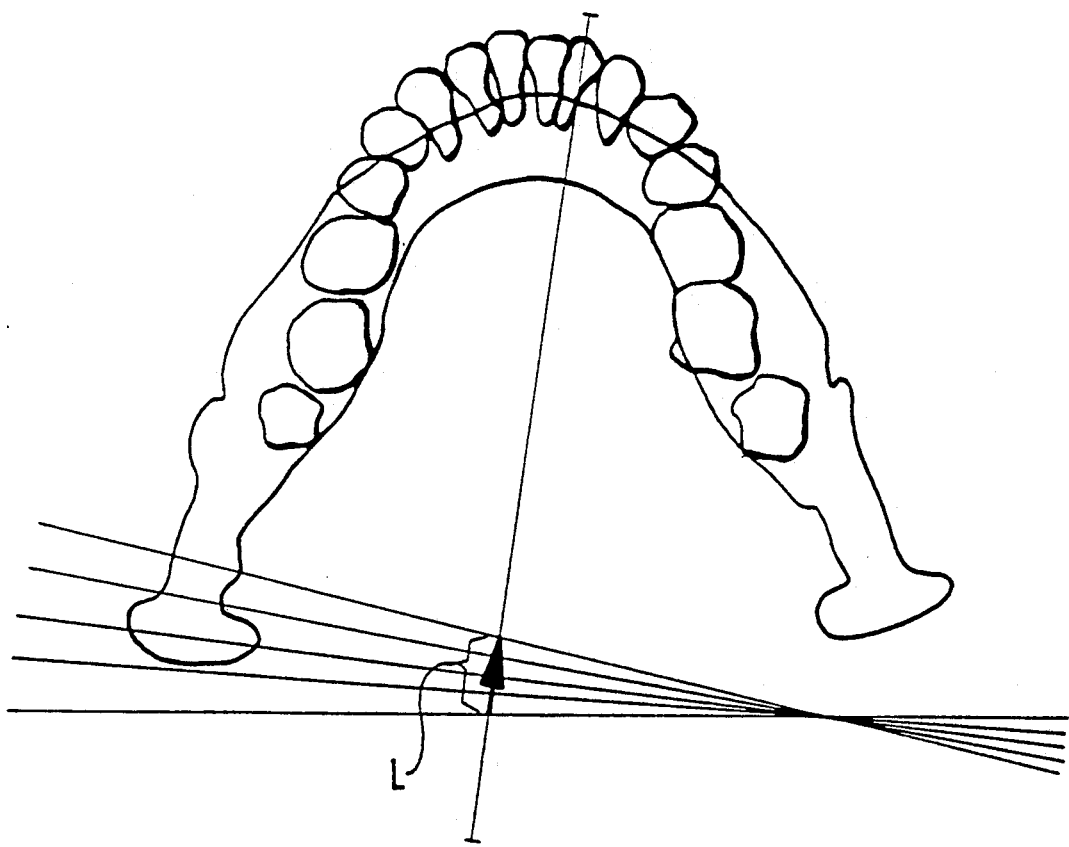
FIG. 6 shows the optimal direction and length for translatory motion in the lateral imaging of posteronaterior.
Figure 7:
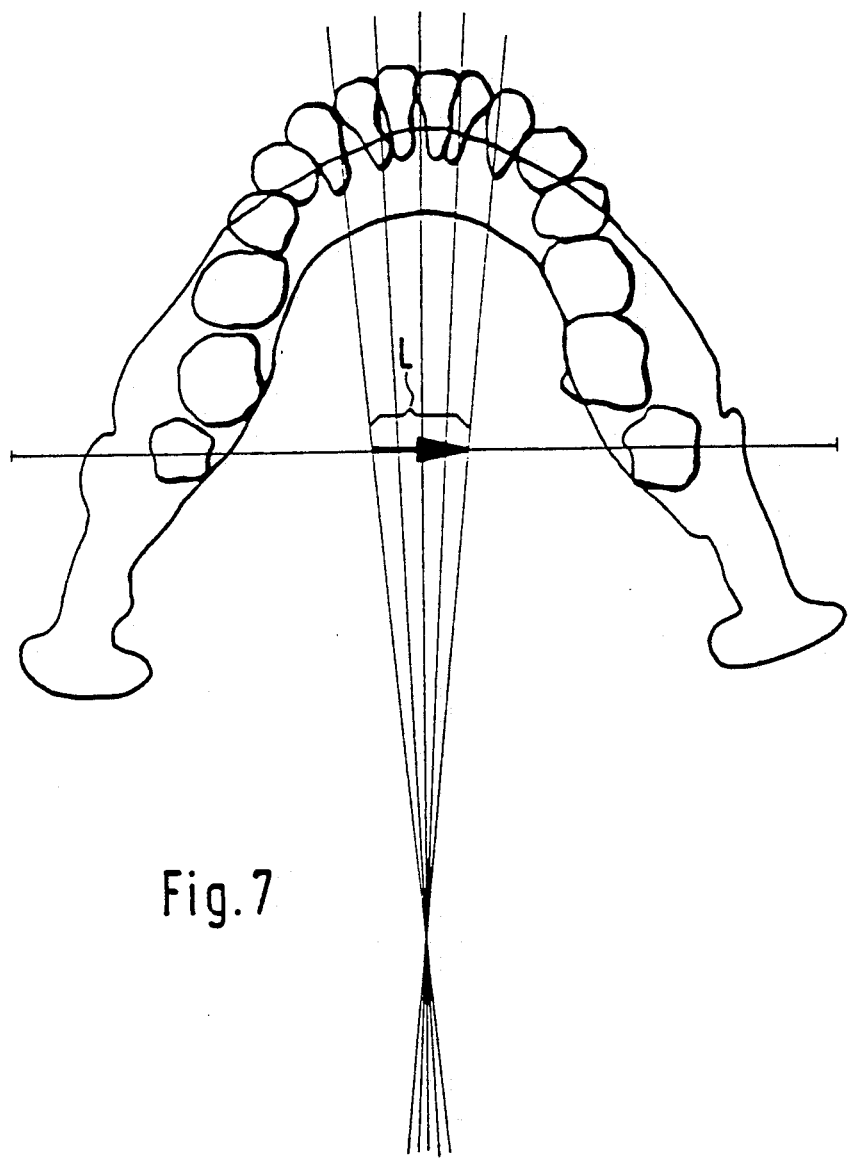
FIG. 7 shows the optimal direction and length for translatory motion in the imaging of front teeth.

The arrangement shown in FIG. 1a employs an instrument, wherein extremely thin metal plates are placed on an average image layer curve. The instrument is accurately set in place of a patient and imaged on film. As a result of the angular positions of the plates (FIG. 1b) it is possible to see and measure the deviation of the direction of ray from orthogonal relative to the normal of the image layer curve. FIG. 2 illustrates the measuring results from the arrangement of FIG. 1 as a graph with the angle of rotation depicted on the horizontal axis and the angle between a cone of rays and and the normal of an image layer depicted on the vertical axis. The figure shows the angles of deviation as positive whenever the cone of rays deflects from normal in the direction of a patient's nose (in FIG. 1a) in the direction of y-axis. According to FIG. 3, in conventional panoramic imaging, the centre of rotating motion travels linearly in the direction of the axis of symmetry of a dental arch. FIGS. 4-7 illustrate the optimal direction and length of said linear or translatory motion for imaging various parts of a dental arch.

Figure 8:
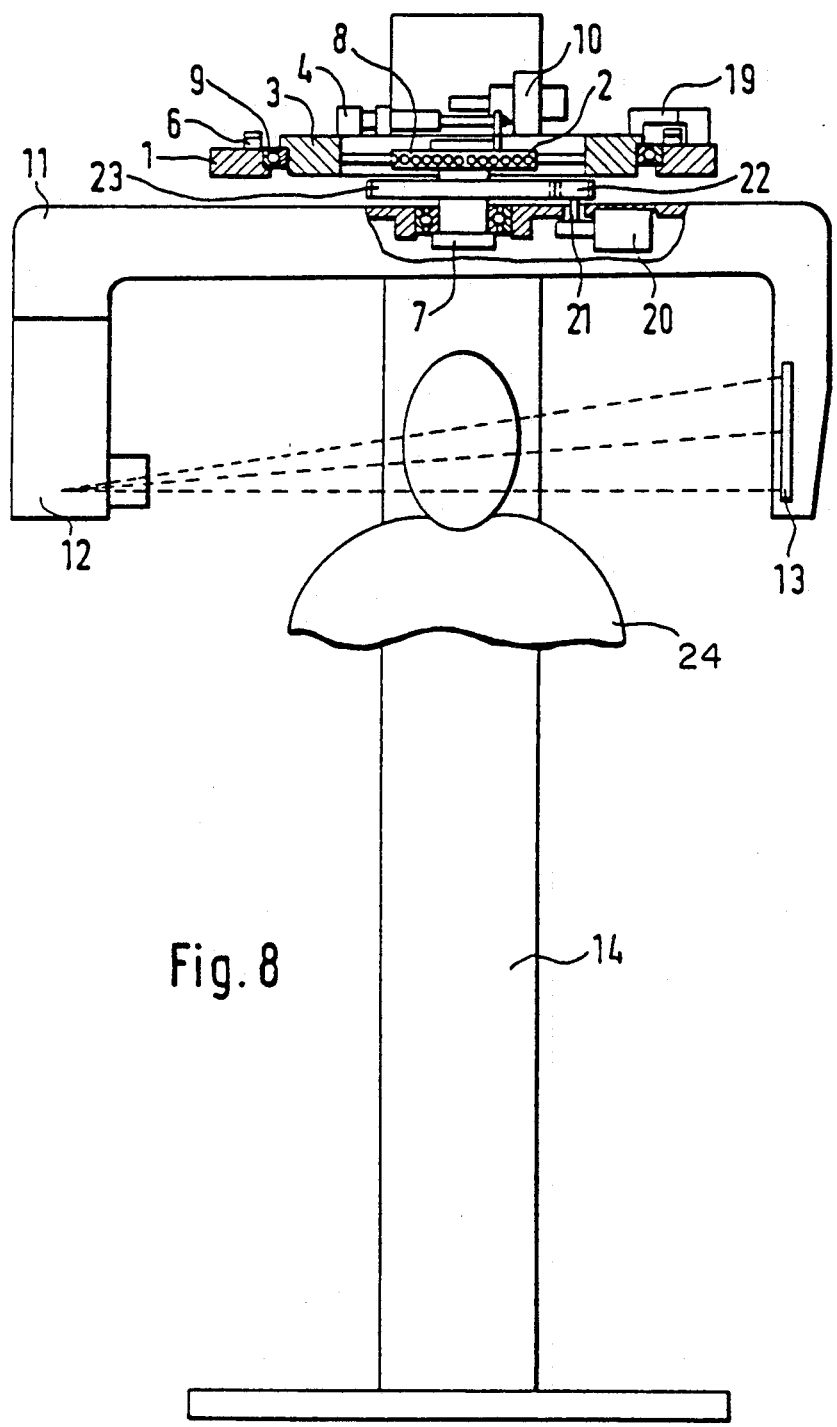
FIG. 8 shows one embodiment of the apparatus.
Figure 9:
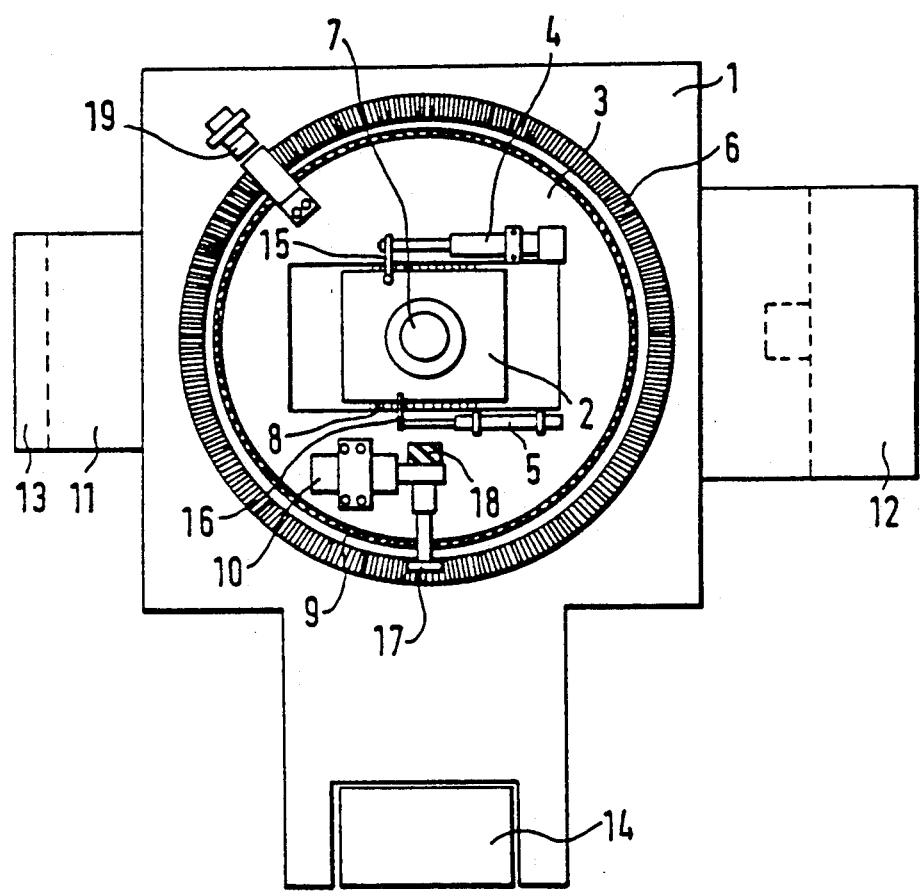
FIG. 9 shows the embodiment of FIG. 8 in plan view.

According to FIGS. 8 and 9, an apparatus of the invention for producing panoramic X-ray image projections comprises a body section 1 which carries a rotary plate 3 suspended through the intermediary of a bearing 9. The rotary plate 3 is in turn provided with a linear plate 2 suspended through the intermediary of a bearing 8, said linear plate carrying a source of X-radiation 12 and an image forming means 13 through the intermediary of a bearing axle 7 and a supporting arm 11. The rotary plate 3 is fitted with a motor 4 for moving said linear plate 2 through the intermediary of a ball screw or the like and a clamping arm 15. The position of linear plate 2 relative to rotary plate 3 is measured by means of a linear sensor 5 through the intermediary of a rod 16. For turning the rotary plate 3 to a desired angular position relative to body 1, said rotary plate is provided with a motor 10 which is fitted with a self-locking worm gear and which, through the action of a pinion 17 and a tooth rim 6 provided on body section 1, changes the angular position of rotary plate 3 and at the same time that of linear plate 2 relative to an object 24 to be imaged. For measuring this angular position, the apparatus is preferably provided with a sensor 18 and a sensor 19 for determining the 0-point of the angular position.

The rotating motion of supporting arm 11 around axle 7 is accomplished e.g. by means of a motor 20 carried by supporting arm 1 and rotating, through the action of a rod 21 and a pinion 22, around a pinion 23 mounted on axle 7. In the illustrated embodiment, the apparatus is fixed by its body section 1 to a frame pipe 14.

We claim:

1. An apparatus for producing panoramic X-ray image projections from a certain section of a dental arch shaped object, said apparatus comprising a fixed body (1), a movable supporting arm (11) whose opposite ends are fitted with an X-ray source (12) and a film holder (13) on the opposite sides of an object (24) to be imaged, means (2014 23) for setting supporting arm (11) in a rotating motion around the object, and means (2, 4, 15) for setting the centre of this rotating motion in a linear movement in dependence on the angular position of supporting arm (11), characterized in that the apparatus further includes means (3, 6, 10) for selecting the direction of linear motion (translatory motion).

2. An apparatus as set forth in claim 1, characterized in that said selection means include: a rotary plate (3), which is journalled (9) to body (1) and to which is journalled (8) a linear plate (2) for facilitating the linear motion; a motor (10), which is carried by rotary plate (3) and which, by means of its associated pinion (17) and a tooth rim (6) provided on body (1), translates rotary plate (3) to a desired angular position; and means (18, 19) for the determination of an angular position.

3. An apparatus as set forth in claim 1, characterized in that said means for producing rotating motion include a motor (20), which is mounted on supporting arm (11) and which, through the action of pinions, rotates around a bearing axle (7), said bearing axle (7) determining the centre of rotating motion.

4. An apparatus as set forth in any of claim 1 characterized in that said means for producing linear motion include: a linear plate (2) to which said axle (7) is fixed and which linear plate is journalled to rotary plate (3), and a motor (4) mounted on rotary plate (3) for translating linear plate (2) relative to rotary plate (3) by means of a rod (15).

* * * * *